United States Patent [19]

Caspar et al.

[11] Patent Number: 5,669,915
[45] Date of Patent: Sep. 23, 1997

[54] DRILLING JIG FOR SURGICAL DRILLING TOOLS

[75] Inventors: Wolfhard Caspar, Contwig; Gebhard Herrmann, Irndorf; Thoedor Lutze, Balgheim; Dieter Weisshaupt, Immendingen, all of Germany

[73] Assignee: Aesculap AG, Tuttlingen, Germany

[21] Appl. No.: 620,392

[22] Filed: Mar. 22, 1996

[30] Foreign Application Priority Data

Mar. 22, 1995 [DE] Germany ............... 195 10 372.6

[51] Int. Cl.⁶ .................................. A61B 17/17
[52] U.S. Cl. ................ 606/96; 606/80; 606/86; 408/202
[58] Field of Search .................. 606/80, 96, 97, 606/98, 172; 408/113, 202

[56] References Cited

U.S. PATENT DOCUMENTS

| 569,896 | 10/1896 | Cauwenberg | 408/202 |
| 1,831,813 | 11/1931 | Levedahl | 408/81 |
| 2,529,988 | 11/1950 | Zempel | 408/110 |
| 2,823,563 | 2/1958 | Nipken | 408/110 |
| 3,017,643 | 1/1962 | Lehde, Jr. | 408/202 |
| 4,788,970 | 12/1988 | Kara et al. | 606/96 |
| 5,409,493 | 4/1995 | Greenberg | 606/96 |

FOREIGN PATENT DOCUMENTS

| 460 447 A1 | 12/1991 | European Pat. Off. . |
| 29 06 068 C2 | 6/1980 | Germany . |
| 29 06 054 A1 | 6/1980 | Germany . |
| 40 16 704 C1 | 9/1991 | Germany . |
| 1 448 111 | 9/1976 | United Kingdom . |

Primary Examiner—Michael Buiz
Assistant Examiner—David O. Reip
Attorney, Agent, or Firm—Barry R. Lipsitz; Ralph F. Hoppin

[57] ABSTRACT

A drilling jig for surgical drilling tools is disclosed. The drilling jig comprises two sleeves of identical design mounted alongside each other on a common holder, with each sleeve being mounted on the holder so as to be pivotable in relation to each other about an axis of rotation extending perpendicular to their respective longitudinal axes. Each sleeve is hollow to allow a drilling tool to pass through. At the rear end of each sleeve is a stop surface for the drilling tool to rest against, the stop surface delimiting the depth to which the drilling tool penetrates the sleeve. Each sleeve is of two-part design and includes a bearing part and an adjusting part, with the bearing part carrying the front end of the sleeve and the adjusting part carrying the stop surface. The bearing part and the adjusting part are threaded to each other in such a manner that the spacing between the stop surface and the front end of the sleeve is adjustable by turning the adjusting part in relation to the bearing part, which enables alteration of the effective length of the sleeve without removing the drilling tool.

13 Claims, 3 Drawing Sheets

DRILLING JIG FOR SURGICAL DRILLING TOOLS

BACKGROUND OF THE INVENTION

The invention relates to a drilling jig for surgical drilling tools comprising a sleeve positionable with its front end on a bone, into which the drilling tool is screwable, thereby passing through the interior of the sleeve, and at the rear end a stop surface for a stop of the drilling tool to rest thereon, the stop delimiting the depth to which the drilling tool penetrates the sleeve, and means for adjusting the spacing between the stop surface and the front end of the sleeve.

Such drilling jigs are used to prevent a maximum penetration depth of the drilling tool from being exceeded when holes are being drilled in bones. To drill holes with a different depth, it is necessary to alter the effective length of the drilling jig. In known drilling jigs, this is done by making an adjustment in the region of the front end of the sleeve, and to make this adjustment it is necessary to remove the drilling jig from the drilling point. After adjustment of the effective length, the drilling jig has to be positioned at the drilling point again, which makes readjustment necessary. This is not only awkward but also involves the possibility of wrong adjustments.

The object underlying the invention is to so design a generic drilling jig that it is also possible to change its effective length without having to remove the drilling jig from the drilling point.

SUMMARY OF THE INVENTION

This object is accomplished in accordance with the invention with a drilling jig of the kind described at the outset by the sleeve being of two-part design and including a bearing part and an adjusting part, by the bearing part carrying the front end and the adjusting part the stop surface, and by the bearing part and the adjusting part being screwed to each other in such a way that the spacing between the stop surface and the front end of the sleeve is adjustable by turning the adjusting part in relation to the bearing part.

Such a design makes it possible for the operator to turn the adjusting part in relation to the bearing part during the drilling and by thereby altering the screwing of the two parts to also alter the effective length. The drilling jig can remain at the drilling point and the drill in the drilling jig and so readjustment is not necessary.

In principle, the adjusting part could be screwed by way of the bearing part, but, in accordance with a preferred embodiment, it is advantageous for the adjusting part to be screwed into the bearing part.

In a particularly preferred embodiment of the invention, provision is made for the screw-in direction of the adjusting part to be the reverse of the turning direction of the drilling tool. Therefore, with a drilling tool normally operating in the clockwise direction an adjusting part with a left-handed thread is used. When turned in the clockwise direction, the adjusting part is moved away from the bearing part and so the effective length of the drilling jig is increased. It is thereby ensured that in the event the adjusting part is taken along unintentionally by the rotating drilling tool, the effective length of the drilling jig cannot be reduced but, at the most, is increased. Therefore, the possibility of too deep a hole being drilled in the event of such unintentional adjustment is excluded.

Provision is preferably made for the adjusting part to be fixable in certain angular positions in relation to the bearing part. Unintentional adjustment of the adjusting part by the drilling tool can thereby be prevented or at least made difficult.

Such fixing can be carried out by, for example, a clamping device. In a preferred embodiment, however, provision is made for the adjusting part to be fixable by an elastic detent device in certain angular positions in relation to the bearing part. This does not provide a completely secure fixing as the elastic detention can be eliminated when a certain force is exceeded, but, with this embodiment, it is, on the other hand, not necessary for the operator to make any additional manipulations to fix the adjusting part. Such fixing by means of an elastic detent device occurs automatically when the adjusting part is turned.

In particular, provision may be made for the elastic detention to be carried out by a detent body on one part being elastically moveable in the radial direction and snapping into recesses on the other part which are spaced along the circumference of the other part. It is thus possible to fix adjusting part and bearing part in different angular positions in relation to one another.

The recesses can be formed, for example, by longitudinal grooves on the circumference of the other part.

It is also advantageous for a depth scale to be arranged on the adjusting part. The operator can then read off the effective length of the drilling jig directly from this depth scale.

In a further preferred embodiment, provision is made for the adjusting part to have a flattened part on its side at its rear end. This flattened part can be identified by the operator by touch and he can thereby feel the respective angular position of the adjusting part. It is thus readily possible, for example, for the operator to turn the adjusting part exactly through one or two rotations and adjust the effective length by a precisely known amount without having to take an exact reading from the depth scale.

It is expedient for the adjusting part to carry a grip part with a profiled circumferential surface. This facilitates turning of the adjusting part relative to the bearing part.

In accordance with a preferred embodiment, the turning is facilitated by the external circumference of the grip part being larger than the external circumference of the adjusting part. In particular, in such an embodiment provision may be made for the grip part to have on its side a flattened part which serves as surface for feeling the angular position.

The drilling jig described hereinabove can be used as a single part for drilling a single hole, but, in a preferred embodiment, provision is made for the drilling jig to include two sleeves of identical design alongside each other on a common holder. It is also possible for several such sleeves to be fixed on a common holder. This makes it possible for a larger number of drilling positions which are, for example, necessary for fixing a bone plate on a bone to be defined by different sleeves, but with only a single instrument being necessary and having to be placed in position once. The individual sleeves can then be adjusted individually to the desired length, and the operator can successively drill the holes to the desired depth by inserting the drilling tool into the sleeves arranged alongside one another.

Herein it is expedient for the sleeves to be mounted on the holder so as to be pivotable in relation to each other about an axis of rotation extending perpendicular to their longitudinal axis. This makes it possible for the sleeves to also be placed at drilling points whose spacing differs slightly from the mutual spacing of the drill sleeves.

In a preferred embodiment, this pivotability of the sleeves is selected such that the sleeves are always oriented with their tips directed towards one another. Therefore, the sleeves are not pivotable to the extent that they stand completely parallel. In any case, the holes are thus drilled so as to extend at an incline to one another, and the screws screwed into these drilled holes thereby secure a bone plate fixed on the bone against displacement in relation to the bone surface.

The following description of preferred embodiments of the invention serves in conjunction with the drawings to explain the invention in greater detail.

DETAILED DESCRIPTION OF THE INVENTION

Figure 1:
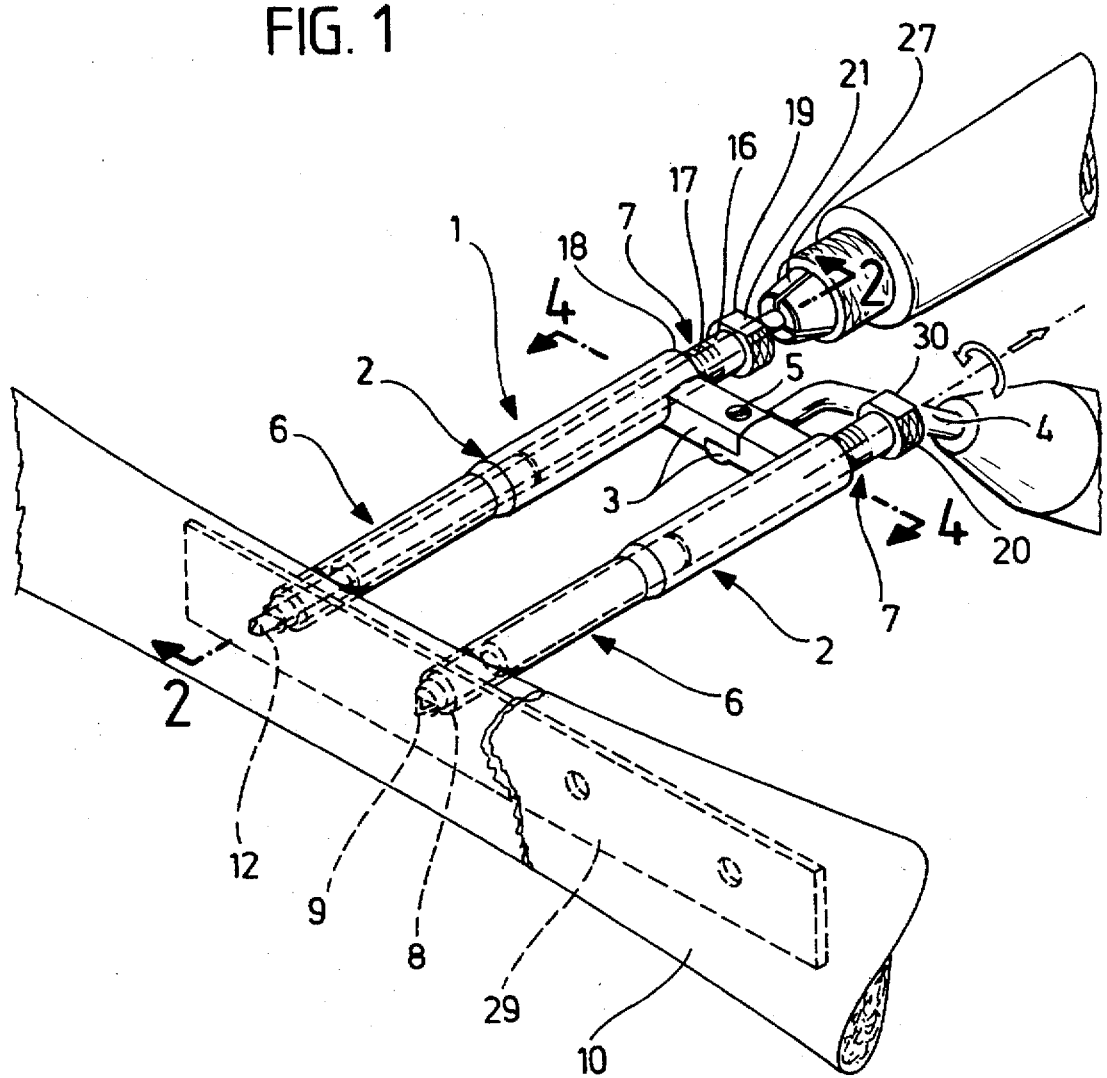
FIG. 1 a drilling jig positioned on a bone, with two sleeves thereof arranged adjacent to one another and a drilling tool inserted in one of these sleeves.
Figure 2:
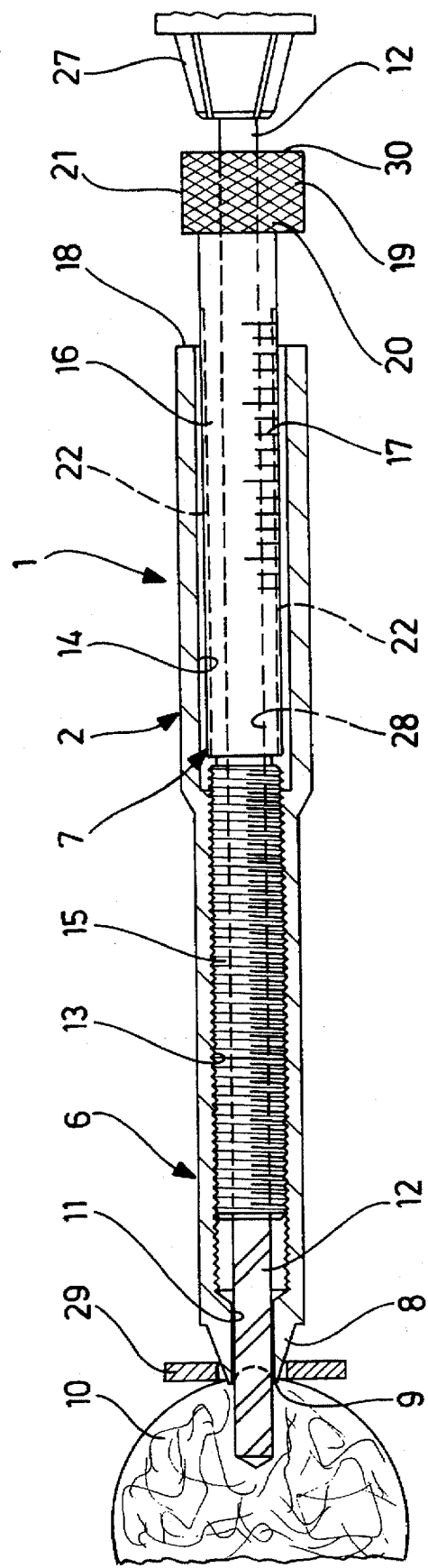
FIG. 2 a sectional view taken along line 2–2 in FIG. 1.
Figure 3:
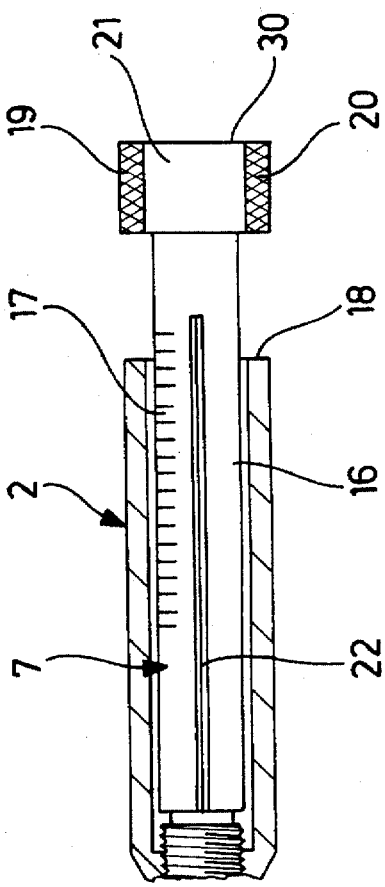
FIG. 3 a partial view of the drilling jig of FIG. 2, in which the adjusting part is turned in relation to the illustration in FIG. 2.
Figure 4:
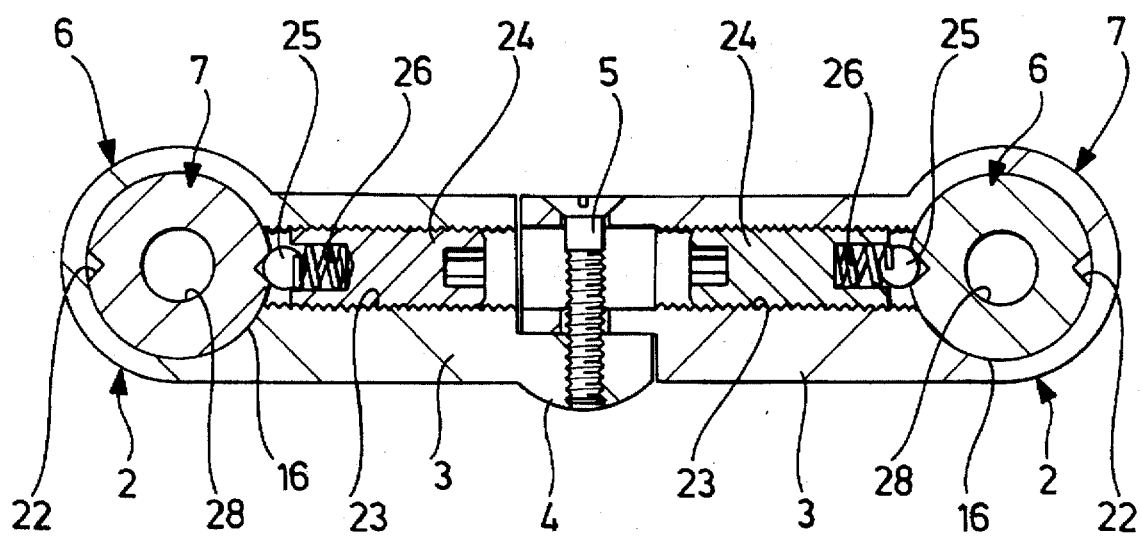
FIG. 4 a sectional view taken along line 4–4 in FIG. 1.

The drilling jig 1 illustrated in the drawings comprises two sleeves 2 of identical design. The sleeves 2 extend essentially parallel to each other and are attached alongside one another by radially protruding arms 3 to a holder 4. One of the arms 3 is integrally joined to the holder 4. The other arm 3 is pivotable about an axis of rotation in relation to the first arm 3. The axis of rotation extends perpendicular to the plane formed by the two sleeves 2. This axis of rotation is formed by a screw 5 which passes through both arms 3. The arms 3 are only pivotable relative to each other within a narrow angular range, more specifically, such that the sleeves 2 never extend exactly parallel, but are always at a slight incline to each other.

As the two sleeves 2 are of completely identical design, only one of these sleeves will be explained in greater detail hereinbelow. This sleeve 2 comprises a likewise sleeve-shaped bearing part 6 and a sleeve-shaped adjusting part 7 screwed into the bearing part 6. At its front end 8, which is of conically tapering design, the bearing part 6 carries two diametrically opposed tips 9, with which the bearing part 6 can be positioned on the surface of a bone 10. In the region of the front end 8, the bearing part 6 has a longitudinal bore 11, the inner diameter of which is slightly larger than the outer diameter of a drilling tool 12, for example, a twist drill.

The longitudinal bore 11 continues into a cylindrical, widened internal threaded space 13, which extends approximately over half of the length of the bearing part 6 and then opens into a widened cylinder space 14 which extends as far as the rear end of the bearing part 6.

The adjusting part 7 is screwed with a front screw-in section 15 in the region of the internal threaded space 13 to the bearing part 6. A cylindrical shaft section 16 adjoining the screw-in section 15 dips into the cylinder space 14 of the bearing part 6 and protrudes over the rear end of the bearing part 6 out of the latter. The shaft section 16 carries a depth scale 17 which slides past the edge 18 of the rear end of the bearing part 6 when the adjusting part 7 is turned so the penetration depth of the adjusting part 7 in the bearing part 6 can be read off at this edge.

At the rear end, the shaft section 16 continues into a disk-shaped grip part 19, the circumferential surface of which is provided with a profile, for example, knurling 20.

The grip part 19 is flattened on one side, with the flattened part 21 extending over, for example, an angle of almost 90° in the circumferential direction.

Arranged in the shaft section 16 of the adjusting part 7 are two longitudinal circumferential grooves 22 which are diametrically opposed to one another and extend over a large part of the length of the shaft section 16.

In the arms 3, detent screws 24 are screwed into threaded bores 23 extending transversely to the longitudinal direction of the bearing part 6. At their free end, the detent screws press a spherical detent body 25 by means of a helical spring 26 against the circumference of the shaft section 16. When the adjusting part 7 is turned in relation to the bearing part 6, with which the arms 3 are in contact, the detent body 25, therefore, snaps elastically into the longitudinal circumferential grooves 22, in each case, in a precisely defined angular position. The adjusting part 7 is thereby fixed in a definite angular position in the bearing part 6 and can only be turned by a certain torque being overcome.

The internal threaded space 13 and the screw-in section 15 carry a left-handed thread. When the adjusting part 7 is turned in the clockwise direction, the adjusting part 7 is, therefore, screwed out of the bearing part 6. The drilling tool 12, on the other hand, which can be inserted into a conventional chuck 27 of a drill, is turned in the clockwise direction in order to drill.

This drilling tool 12 extends through a through-bore 28 in the adjusting part 7. The internal diameter of this through-bore 28 is slightly larger than the external diameter of the drilling tool 12, and, therefore, on the one hand, the drilling tool 12 is guided precisely, while, on the other hand, so much play remains that the drilling tool 12 does not normally take along and turn the adjusting part 7 with it.

To drill a hole in a bone 10, the drilling points are marked exactly by, for example, placing a bone plate 29 thereat. The two sleeves 2 of the drilling jig 1 are guided through holes in the bone plate 29 and pressed against the surface of the bone 10, and the sleeves are fixed in this position by the tips 9.

The operator then sets the desired drilling depth individually for each hole to be drilled by turning the adjusting part 7 in relation to the bearing part 6. The spacing of the grip part 19 from the tips 9 is thereby adjusted. By feeling the flattened part 21, the operator can sense the number of rotations of the adjusting part 7. The fixing of the adjusting part 7 by the detent body 25 while it is being turned in the bearing part 6 is also an orientation aid to him as renewed fixing always occurs after a rotation through 180°.

Once the desired effective length of the respective sleeve has been set, the operator guides the drilling tool 12 through the through-bore 28 and the longitudinal bore 11 in alignment with it and drills to the desired depth. The chuck 27 then strikes the end surface 30 of the grip part 19 and prevents a larger drilling depth.

If the operator wishes to drill a deeper hole during this drilling operation he can do so, with the drilling tool inserted and the drilling jig 1 positioned, by simply screwing the adjusting part 7 in relation to the bearing part 6. The drilling operation can be continued immediately after this screw adjustment. Readjustment or even repositioning of the drilling jig is not necessary.

What is claimed is:

1. Drilling jig for a surgical drilling tool, comprising:
   two sleeves of identical design alongside each other on a common holder;
   each sleeve being mounted on said holder so as to be pivotable in relation to each other about an axis of rotation extending perpendicular to their longitudinal axis;

each of said sleeves being positionable with its front end on a bone, into which the drilling tool is screwable, thereby passing through the interior of said sleeve, and at the rear end a stop surface for a stop of said drilling tool to rest thereon, said stop delimiting the depth to which said drilling tool penetrates said sleeve; and means for adjusting the spacing between said stop surface and said front end of said sleeve, wherein:

said sleeve is of two-part design and includes a bearing part and an adjusting part, in that said bearing part carries said front end and said adjusting part carries said stop surface, and in that said bearing part and said adjusting part are screwed to each other in such a way that the spacing between said stop surface and said front end of said sleeve is adjustable by turning said adjusting part in relation to said bearing part.

2. Drilling jig as defined in claim 1, characterized in that said adjusting part is screwed into said bearing part.

3. Drilling jig as defined in claim 1, characterized in that the screw-in direction of said adjusting part is the reverse of the turning direction of said drilling tool.

4. Drilling jig as defined in claim 1, characterized in that said adjusting part is fixable in certain angular positions in relation to said bearing part.

5. Drilling jig as defined in claim 4, characterized in that said adjusting part is fixable by an elastic detent means in certain angular positions in relation to said bearing part.

6. Drilling jig as defined in claim 5, characterized in that the elastic detention is effected by a detent body on said bearing part, said detent body being elastically moveable in the radial direction and snapping into recesses on said adjusting part, said recesses being spaced along the circumference of said adjusting part.

7. Drilling jig as defined in claim 6, characterized in that said recesses are formed by longitudinal grooves on the circumference of said adjusting part.

8. Drilling jig as defined in claim 1, characterized in that a depth scale is arranged on said adjusting part.

9. Drilling jig as defined in claim 1, characterized in that said adjusting part has a flattened part on its side at its rear end.

10. Drilling jig as defined in claim 1, characterized in that said adjusting part carries a grip part with a profiled circumferential surface.

11. Drilling jig as defined in claim 10, characterized in that the external circumference of said grip part is larger than the external circumference of said adjusting part.

12. Drilling jig as defined in claim 11, characterized in that said grip part has a flattened part on its side.

13. Drilling jig as defined in claim 14, characterized in that said sleeves are only slightly pivotable about the axis of rotation and are always inclined to each other at a slight angle.

* * * * *